United States Patent [19]

Duffett et al.

[11] Patent Number: Plant 5,989

[45] Date of Patent: May 19, 1987

[54] CHRYSANTHEMUM PLANT NAMED ALLURE

[75] Inventors: William E. Duffett; Cornelis P. VandenBerg, both of Salinas, Calif.; Grace H. Mack, 108 Wahackme Rd., New Canaan, Conn. 06840

[73] Assignee: Grace H. Mack, New Canaan, Conn.

[21] Appl. No.: 769,737

[22] Filed: Aug. 27, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Allure having flat capitulum form; daisy capitulum type; yellow ray floret color; diameter across face of capitulum up to 8 cm.; short plant height, semi-spreading branching pattern; average natural season flowering date of September 10 in the West Coast area; average flowering response period of seven weeks in photoperiodic controlled short day programs, and durable, uniform performance in Spring small pot flowering programs.

3 Drawing Figures

The present invention comprises a new and distinct cultivar of *Chrysanthemum morifolium,* Ramat., named Allure.

Allure is a product of a planned breeding program which had the objective of creating new Chrysanthemum cultivars with daisy capitulum type, short plant height, spreading branching pattern, durable inflorescence, six to seven week flowering response period, and yellow ray floret color under outdoor natural season conditions.

Allure, identified as 82N13005, was originated from a cross made by Grace H. Mack in a controlled breeding program in New Canaan, Conn. in the year 1981. The female parent was an unnamed seedling bred from Wolverine, disclosed in U.S. Plant Pat. No. 4,312, crossed with an unnamed seedling. The male parent was also an unnamed seedling selected from a cross of M702, an unnamed seedling, and Yellow Jacket, disclosed in U.S. Plant Pat. No. 4,244.

Allure was discovered and selected as a flowering plant within the progeny of the stated cross by William E. Duffett in September 1982 in a controlled open area in Salinas, Calif.

The first act of asexual reproduction of Allure was accomplished when vegetative cuttings were taken from the initial selection in February 1983 by Cornelis P. VandenBerg. Horticultural examination of selected units initiated September 1983 has demonstrated that the combination of characteristics as herein disclosed for Allure are firmly fixed and are retained through successive generations of asexual reproduction.

Allure has not been observed under all possible environmental conditions. The phenotype may vary significantly with variations in environment such as temperature, light intensity and day length. The observations, measurements and comparisons describe plants grown in a controlled open area in Salinas, Calif.

Rooted cuttings were established in soil and maintained outdoors under the natural temperature and day length prevailing during July through September. Single pinching was practiced with all branches and buds retained.

The following traits have been repeatedly observed and are determined to be basic characteristics of Allure, which in combination distinguish this Chrysanthemum as a new and distinct cultivar:

(1) Flat capitumum form.

(2) Daisy capitulum type.

(3) Yellow ray floret color.

(4) Diameter across face of capitulum up to 8 cm.

(5) Short plant height.

(6) Semi-spreading branching pattern.

(7) Average natural season flowering date of September 10.

(8) Average flowering response of seven weeks in photoperiodic controlled flowering programs.

(9) Durable, uniform performance in Spring small pot flowering programs.

The accompanying photographic drawings show typical leaf and inflorescence characteristics of Allure.

Sheet 1 is a color photograph of Allure.

Sheet 2 is a black and white photograph of three views of the inflorescence of Allure.

Sheet 3 is a black and white photograph showing the leaves of Allure in three stages of growth (mature, intermediate and immature).

Of the many commercial cultivars known to the present inventors, the most similar existing cultivar in comparison to Allure is the unpatented cultivar Yellow Starlet. Reference is made to attached Chart A which compares certain characteristics of Allure to those same characteristics of Yellow Starlet. Similar traits are color, type and capitulum diameter. Allure differs from Yellow Starlet by having ligulate or flat ray florets rather than a spoon form, an earlier natural season flower date, shorter plant height, and earlier response.

In the following description, color references are made to The Royal Horticultural Society Colour Chart. The color values were determined between 2:15 and 2:30 p.m. on Sept. 14, 1984 under 380 foot-candle light intensity at Salinas, Calif.

Classification:

*Botanical.*—*Chrysanthemum morifolium,* Ramat., cv Allure.

*Commercial.*—Daisy spray pot mum and garden cultivar.

I. INFLORESCENCE

A. Capitulum:

*Form.*—Flat.

*Type.*—Daisy.

*Permanence.*—Approximately 10 days.

*Diameter across face.*—6 to 8 cm.

B. Corolla of ray florets:

*Color (general tonality from a distance of three meters).*—Yellow.

*Color (upper surface).*—6A, 6B to 6C.

*Color (under surface).*—6C.

*Shape.*—Long, narrow. Blunt, rounded tip.

C. Corolla of disc florets:

*Color (mature).*—12A.

*Color (immature).*—154B.

D. Reproductive organs:

*Androecium.*—Present disc florets; abundant pollen.

*Gynoecium.*—Present both ray and disc florets.

II. PLANT

A. General appearance:

*Height.*—Short.

*Branching pattern.*—Semi-spreading.

B. Foliage:

*Color (upper surface).*—147A.

*Color (under surface).*—147B.

*Shape.*—Shallow lobed with slight serration.

CHART A

COMPARISON OF ALLURE AND YELLOW STARLET

| CULTIVAR | CAPITULUM AVERAGE RAY FLORET COLOR | FORM AND TYPE | NATURAL SEASON DATE | PLANT HEIGHT |
|---|---|---|---|---|
| ALLURE | YELLOW | FLAT DAISY | SEPTEMBER 10 | SHORT |
| YELLOW STARLET | YELLOW | SPOON DAISY | SEPTEMBER 20 | TALL |

CHART A-continued

COMPARISON OF ALLURE AND YELLOW STARLET

| CULTIVAR | BRANCHING PATTERN AND SPREAD | DIAMETER ACROSS FACE OF CAPITULUM | PERMANENCE OF FORM AND COLOR | CONTROLLED RESPONSE |
|---|---|---|---|---|
| ALLURE | SEMI-SPREADING | 6 to 8 cm. | 10 DAYS | SEVEN |
| YELLOW STARLET | UPRIGHT | 6 to 8 cm. | 14 DAYS | EIGHT |

COMPARISONS MADE OF PLANTS GROWN UNDER NATURAL SEASON OUTDOOR CONDITIONS IN SALINAS, CALIFORNIA

We claim:

1. A new and distinct cultivar of *Chrysanthemum morifolium,* Ramat., named Allure, as described and illustrated, and particularly characterized as to uniqueness by the combined characteristics of flat capitulum form, daisy capitulum type, yellow ray floret color, diameter across face of capitulum up to 8 cm., short plant height, semi-spreading branching pattern, average natural season flowering date of September 10 in the West Coast area, average flowering response period of seven weeks in photoperiodic controlled short day programs, and durable, uniform performance in Spring small pot flowering programs.

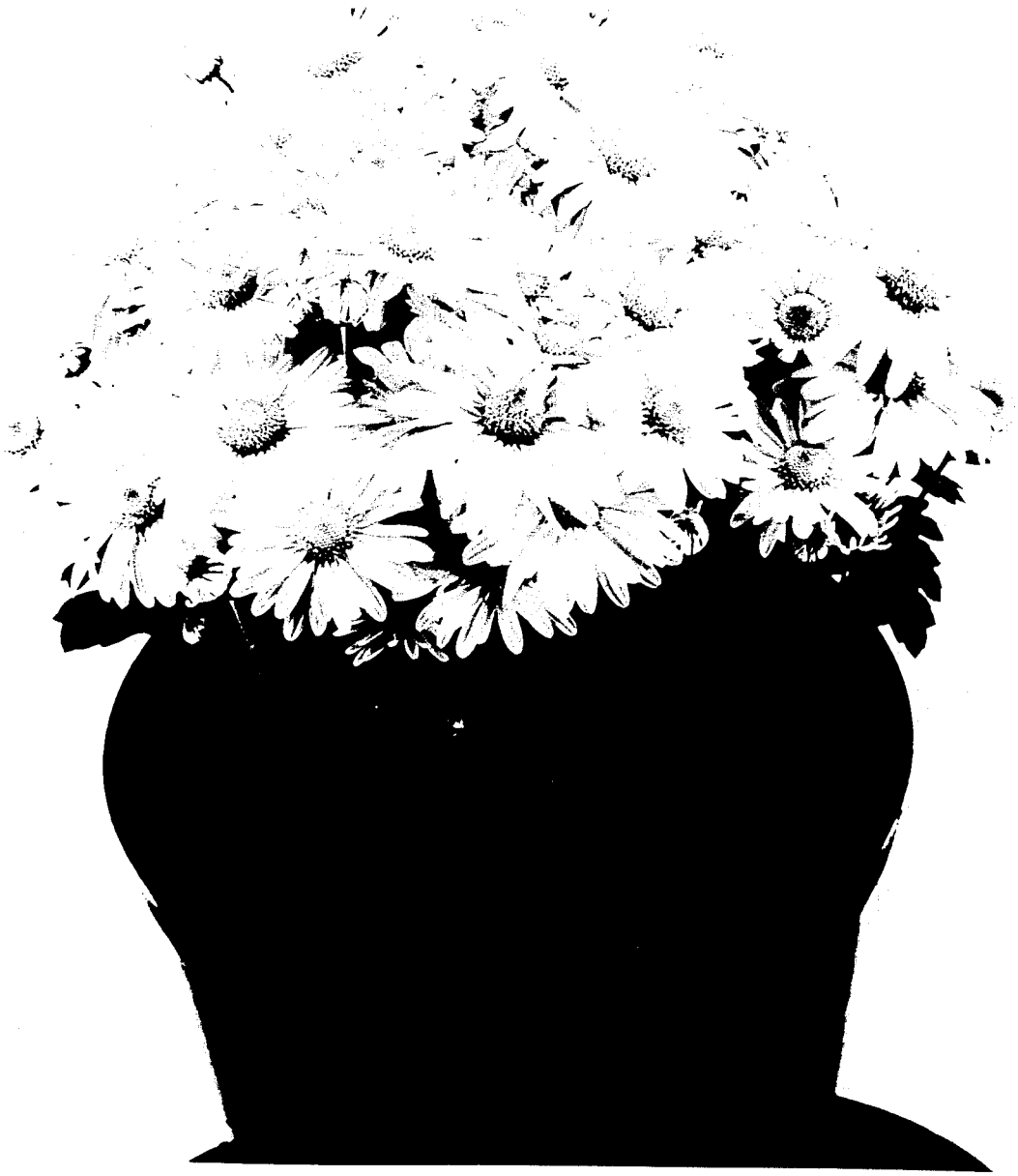

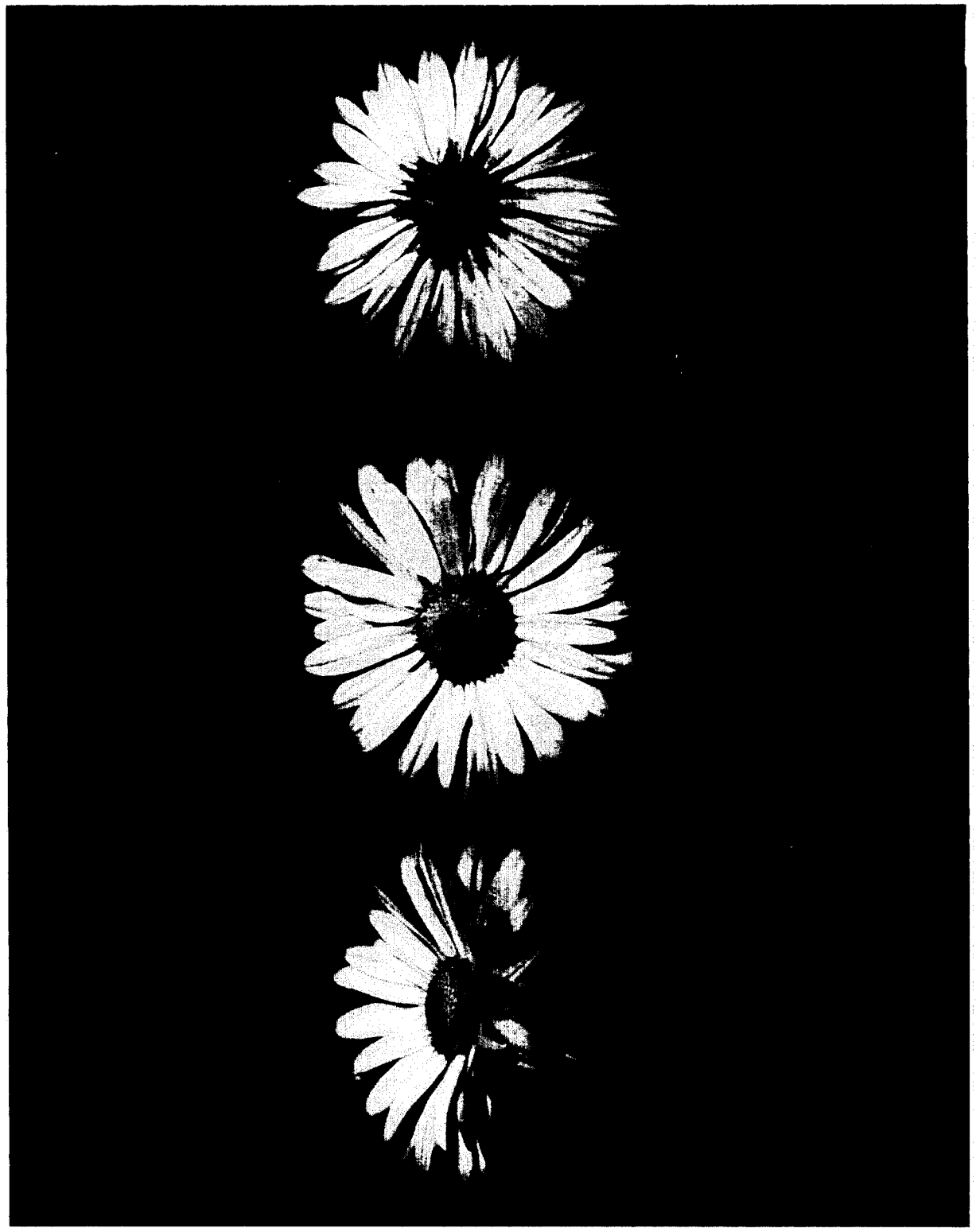

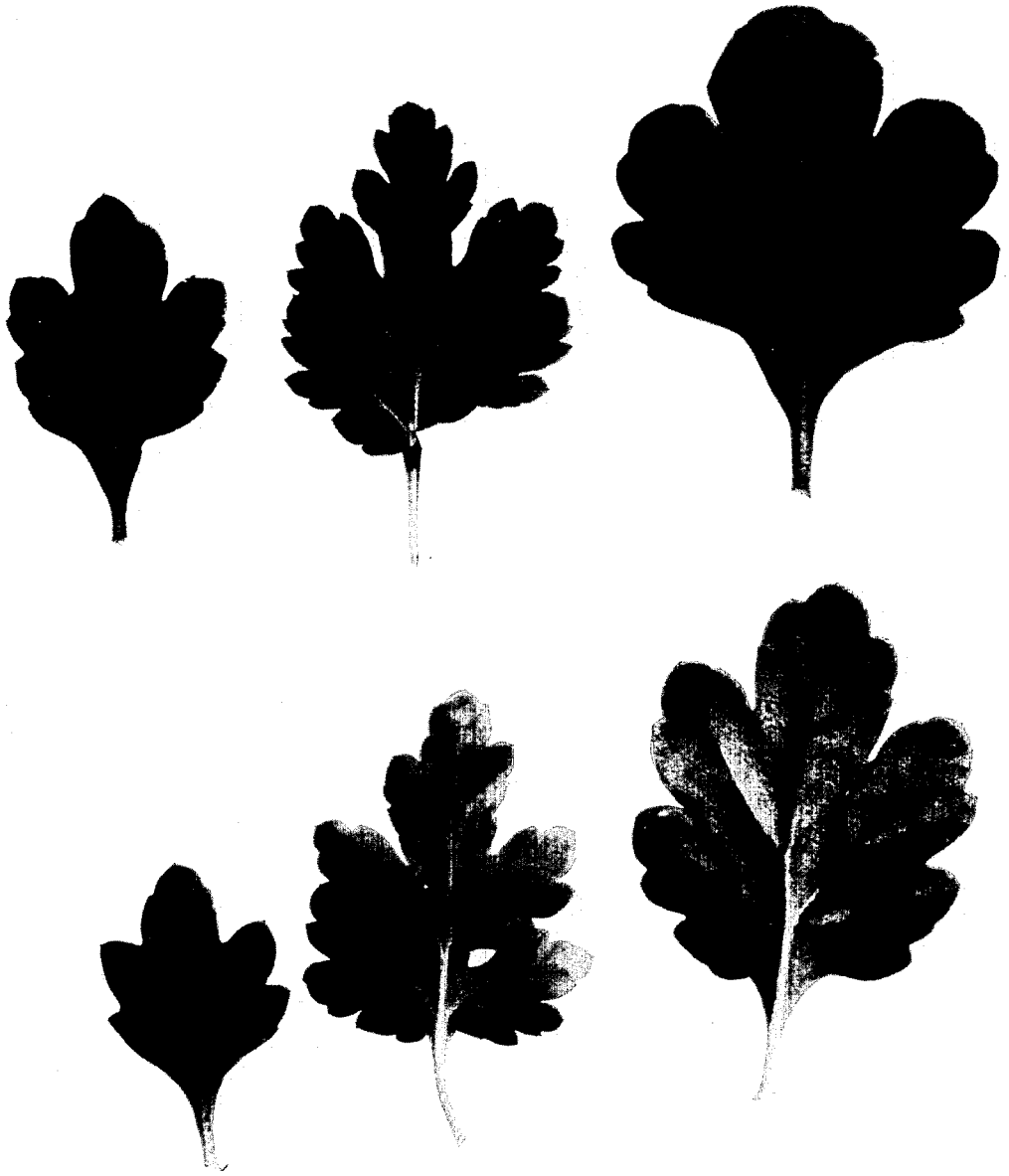

* * * * *